United States Patent
Tran et al.

(10) Patent No.: US 10,391,259 B2
(45) Date of Patent: Aug. 27, 2019

(54) DOSE DIVIDER SYRINGE

(71) Applicant: Teleflex Medical Incorporated, Research Triangle Park, NC (US)

(72) Inventors: Huy Tran, Riverton, UT (US); Perry Croll, Sandy, UT (US)

(73) Assignee: TELEFLEX MEDICAL INCORPORATED, Morrisville, NC (US)

( * ) Notice: Subject to any disclaimer, the term of this patent is extended or adjusted under 35 U.S.C. 154(b) by 703 days.

(21) Appl. No.: 14/561,756

(22) Filed: Dec. 5, 2014

(65) Prior Publication Data

US 2015/0157801 A1    Jun. 11, 2015

Related U.S. Application Data

(60) Provisional application No. 61/912,715, filed on Dec. 6, 2013.

(51) Int. Cl.
*A61M 5/315*      (2006.01)

(52) U.S. Cl.
CPC ........ *A61M 5/31591* (2013.01); *A61M 5/3156* (2013.01); *A61M 5/31553* (2013.01); *A61M 2205/6081* (2013.01)

(58) Field of Classification Search
CPC .... A61M 5/31595; A61M 2005/31591; A61M 5/315
USPC ....................................................... 604/208
See application file for complete search history.

(56) References Cited

U.S. PATENT DOCUMENTS

| | | | |
|---|---|---|---|
| 3,978,858 A | * | 9/1976 | Tischlinger ........... A61M 5/178 222/386 |
| 5,009,645 A | | 4/1991 | Silver et al. |
| 5,318,544 A | | 6/1994 | Drypen et al. |
| 5,601,077 A | | 2/1997 | Imbert |
| 5,662,098 A | | 9/1997 | Yoshida |
| 5,833,669 A | | 11/1998 | Wyrick |
| 5,951,526 A | | 9/1999 | Korisch et al. |
| 5,954,695 A | | 9/1999 | Sims et al. |
| 7,041,085 B2 | | 5/2006 | Perez et al. |
| 7,296,566 B2 | | 11/2007 | Alchas |
| 8,535,277 B2 | | 9/2013 | Oden et al. |

(Continued)

FOREIGN PATENT DOCUMENTS

| | | | |
|---|---|---|---|
| CA | 2 400 937 A1 | 8/2001 | |
| EP | 0208975 A2 | * 1/1987 | ............ A61M 5/315 |

(Continued)

*Primary Examiner* — Edelmira Bosques
(74) *Attorney, Agent, or Firm* — Baker & Hostetler LLP

(57) ABSTRACT

A syringe includes a barrel with an internal surface defining an internal bore therein, a plunger disposed within the internal bore of the barrel, and a dose divider disposed on the plunger. The dose divider includes a first end, a first abutment surface, and a second abutment surface. The first abutment surface is spaced apart from the first end in the axial direction by a first axial distance, and the second abutment surface is spaced apart from the first end in the axial direction by a second axial distance. The second abutment surface is spaced apart from the longitudinal axis of the plunger by a first radial distance, and the first radial distance is greater than a radial dimension from a longitudinal axis of the barrel to the internal surface of the barrel near a proximal end of the barrel.

6 Claims, 9 Drawing Sheets

(56) References Cited

U.S. PATENT DOCUMENTS

| | | |
|---|---|---|
| 2005/0004530 A1 | 1/2005 | Grabenkort et al. |
| 2005/0137532 A1 | 6/2005 | Rolla |
| 2006/0004467 A1 | 1/2006 | Lecomte et al. |
| 2013/0289493 A1 | 10/2013 | Baney et al. |

FOREIGN PATENT DOCUMENTS

| | | | |
|---|---|---|---|
| JP | H05-184674 A | 7/1993 | |
| JP | WO 9532750 A1 * | 12/1995 | ........... B05B 1/3436 |
| JP | H08-47530 A | 2/1996 | |
| WO | 03/004080 A1 | 1/2003 | |
| WO | 2011/073176 A1 | 6/2011 | |

* cited by examiner

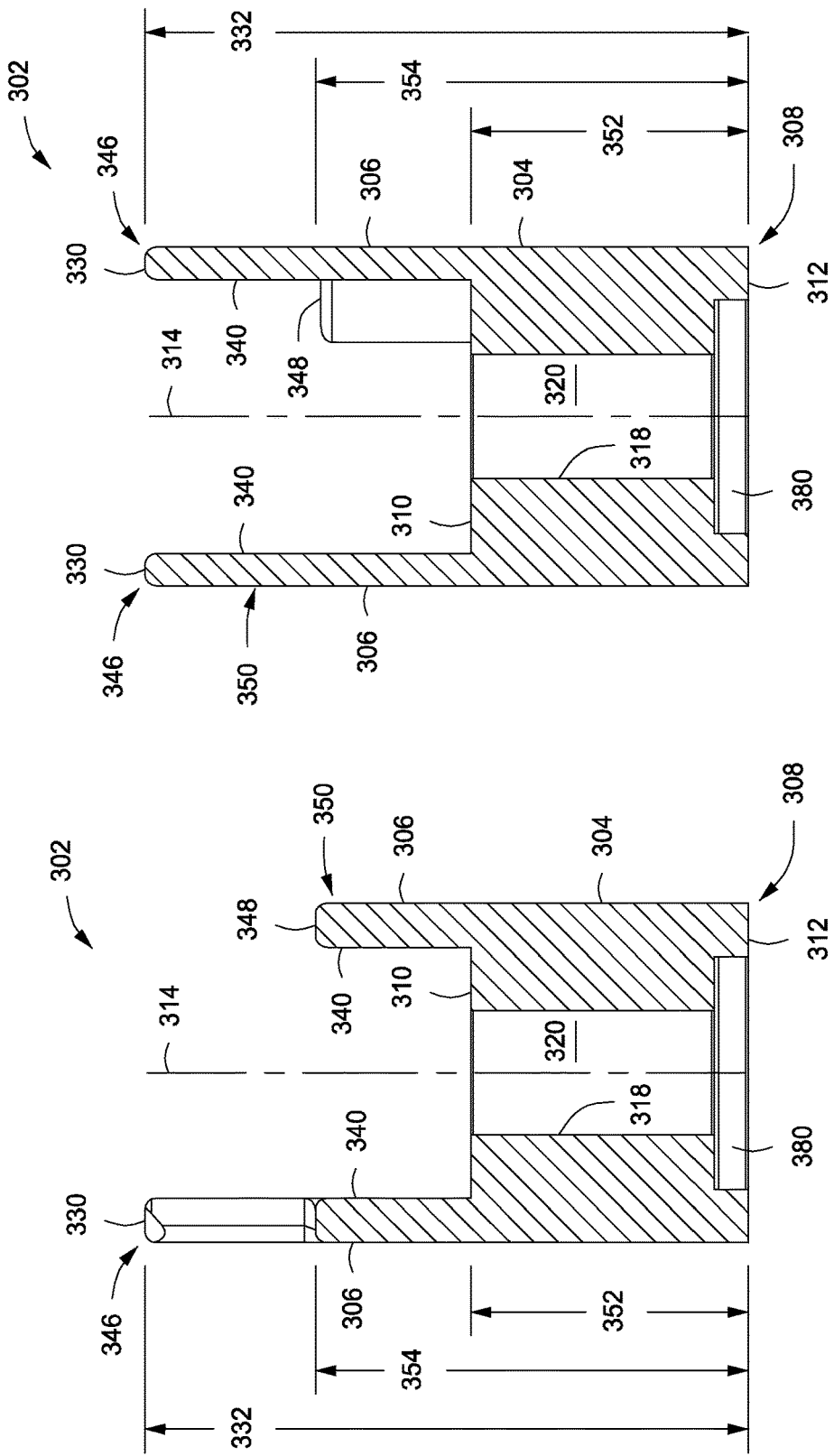

DOSE DIVIDER SYRINGE

CROSS-REFERENCE TO RELATED APPLICATIONS

This application claims priority to U.S. Provisional Patent Application No. 61/912,715, entitled "Dose divider Syringe," filed on Dec. 6, 2013, the disclosure of which is hereby incorporated by reference in its entirety.

TECHNICAL FIELD

This patent disclosure relates generally to syringes and, more particularly, to syringes that provide tactile feedback of a quantity of material delivered by operation thereof.

BACKGROUND

Syringes are known for storing and transporting substances with fluid properties such as gases, liquids, pastes, slurries, and the like. A syringe may include a barrel defining a bore in communication with a port, and a piston disposed within the barrel. Translation of the piston away from the port may draw material into the barrel through the port. Alternatively, translation of the piston toward the bore may expel material from the barrel out of the port.

A syringe barrel may be formed from a transparent or translucent material, such that a position of the piston within the bore is visible through the barrel. Further, the syringe barrel may include indicia disposed thereon, such that longitudinal alignment of the piston relative to the indicia may visually indicate a volume of material stored between the piston and the port.

U.S. Pat. No. 5,009,645 (hereinafter, "the '645 patent") purports to describe a syringe for dispensing measured quantities of a material (e.g., a medicament). The syringe from the '645 patent includes a barrel, a plunger rod having a cruciform transverse cross section, and an infinitely adjustable stop member secured to the plunger rod for positively setting the length of travel of the plunger rod to thereby control the volume of material dispensed from the syringe. However, sequential delivery of multiple doses using the syringe from the '645 patent may be subject to dosage errors resulting from inaccurate displacement of the infinitely adjustable stop member between dose deliveries, undue time consumption to adjust the position of the infinitely adjustable stop member, or both.

U.S. Pat. No. 5,601,077 (hereinafter, "the '077 patent") purports to describe a syringe with a dose limiting housing for preventing delivery of a predetermined amount of liquid from the syringe by limiting a travel of a plunger within a barrel of the syringe. The '077 patent states that the dose limiting housing is adapted to interact between a radially extending projection on the plunger rod, such as a flange, and a proximal end of the syringe barrel, which includes a barrel flange, to limit the distal motion of the plunger rod with respect to the barrel. However, the dose limiting housing of the '077 patent may effect delineation of no more than two distinct ranges of plunger travel, corresponding to the housing installed on the syringe and the housing removed from the syringe, because the dose limiting housing has only two axial bearing surfaces.

U.S. Pat. No. 5,951,526 (hereinafter, "the '526 patent") purports to describe a nasal syringe in which the travel of the plunger is controlled by a stop mechanism. The syringe of the '526 patent includes a stop coupled to an end cap by a hinge. However, the stop mechanism of the '526 patent may effect delineation of no more than two distinct ranges of plunger travel corresponding to an interfering position and a non-interfering position of the stop mechanism about the hinge.

U.S. Patent Publication No. 2005/0137532 (hereinafter, "the '532 publication") purports to describe a unit to administer medication having a plunger with non-reusable stroke stops sequentially arranged along the plunger. According to the '193 patent, the stroke stops are frangible about a weakening line, such that each broken stroke stop enables the forward movement of the impelling plunger and the administration of a corresponding dose. However, the stroke stops of the '532 publication may interfere with filling an empty syringe so configured, and therefore limit application to pre-filled syringes. Further, the stroke stops of the '532 patent are inherently non-reusable because of their frangible nature, and the stroke stops may be complex and expensive to manufacture.

U.S. Pat. No. 5,318,544 (hereinafter "the '544 patent") purports to describe a syringe for metering predetermined volumes of fluid therefrom. The syringe of the '544 patent includes a tube, a clip, and a metering plunger having stop surfaces disposed thereon, where the plunger is inserted through an opening in the clip and is slidably located within the syringe tube. However, the plunger stop surfaces of the '544 patent have complex shapes and could be difficult or expensive to manufacture. Further, the stop surfaces of the '544 patent may interfere with filling an empty syringe by requiring rotation of the plunger in addition to axial translation during a ruling step.

U.S. Patent Publication No. 2003/0004467 (hereinafter "the '467 publication") purports to describe a multi-dose syringe allowing sequential injection of identical or non-identical volumes. A plurality of stops are arranged at various axial and azimuthal locations about a plunger shaft of the '467 publication, such that the stops may axially interfere with or pass through a screw knob disposed depending on azimuthal alignment of the plunger shaft with the screw knob. However, the plunger stops of the '467 publication have complex shapes that may be difficult or expensive to manufacture. Further, the plunger stops of the '467 publication may interfere with filling an empty syringe by requiring rotation of the plunger in addition to axial translation during a filling step.

Accordingly, there is a need for an improved syringe that enables accurate delineation of more than two ranges of plunger translation relative to a barrel, that facilitates filling of an empty syringe so configured, and that s simple and inexpensive to manufacture.

SUMMARY

According to an aspect of the disclosure, a syringe includes a barrel having an internal surface defining an internal bore therein, a plunger disposed within the internal bore of the barrel, and a dose divider disposed on the plunger. The dose divider includes a first end, a first abutment surface facing an axial direction along a longitudinal axis of the plunger, the first abutment surface being spaced apart from the first end in the axial direction by a first axial distance, and a second abutment surface facing the axial direction, the second abutment surface being spaced apart from the first end in the axial direction by a second axial distance, the second axial distance being greater than the first axial distance, the second abutment surface being spaced apart from the longitudinal axis of the plunger by a first radial distance. The first radial distance is greater than a radial dimension from a longitudinal axis of the barrel to the internal surface of the barrel near a proximal end of the barrel.

According to an aspect of the disclosure, a method for delivering a material using a syringe includes loading the material into an internal bore of a barrel, expelling a first portion of the material from a distal port of the barrel by translating a plunger toward the distal port of the barrel until a first abutment surface of a dose divider bears on a flange of the barrel at a first radial location outside the internal bore of the barrel, rotating the dose divider about a longitudinal axis of the plunger from a first azimuthal location to a second azimuthal location relative to the barrel, and expelling a second portion of the material from the distal port of the barrel by translating the plunger toward the distal port of the barrel until a second abutment surface of the dose divider bears on the flange of the barrel at a second radial location outside the internal bore of the barrel.

According to an aspect of the disclosure, a method for delivering a material using a syringe includes loading the material into an internal bore of a barrel, expelling a first portion of the material from a distal port of the barrel by translating a plunger toward the distal port of the barrel until a dose divider bears on a flange of the barrel at a first radial location outside the internal bore of the barrel, and a first abutment surface of the dose divider bears on a flange of the plunger, rotating the dose divider about a longitudinal axis of the plunger from a first circumferential location to a second circumferential location relative to the barrel, and expelling a second portion of the material from the distal port of the barrel by translating the plunger toward the distal port of the barrel until a second abutment surface of the dose divider bears on the flange of the plunger.

According to an aspect of the disclosure, a syringe kit includes a barrel having an internal surface defining an internal bore therein, a plunger having a piston disposed at a distal end of the plunger, the piston configured to translate within the internal bore of the barrel with sliding and sealing engagement, and a dose divider configured to couple with the plunger. The dose divider includes a first end, a first abutment surface facing an axial direction along the longitudinal axis of the plunger, the first abutment surface being spaced apart from the first end in the axial direction by a first axial distance, and a second abutment surface facing the axial direction, the second abutment surface being spaced apart from the first end in the axial direction by a second axial distance, the second axial distance being greater than the first axial distance, the second abutment surface being spaced apart from the longitudinal axis of the plunger by a first radial distance. The first radial distance is greater than a radial dimension from the longitudinal axis of the barrel to the internal surface of the barrel near a proximal end of the barrel.

According to an aspect of the disclosure, a plunger for a syringe includes a shaft disposed along a longitudinal axis, a piston disposed at a distal end of the plunger, and a dose divider disposed on the shaft. The dose divider includes a first end, a first abutment surface facing an axial direction along the longitudinal axis, the first abutment surface being spaced apart from the first end in the axial direction by a first axial distance, and a second abutment surface facing the axial direction, the second abutment surface being spaced apart from the first end in the axial direction by a second axial distance, the second axial distance being greater than the first axial distance, the second abutment surface being spaced apart from the longitudinal axis in a radial direction by a first radial distance, the radial direction being normal to the longitudinal axis. The first radial distance is greater than a radial dimension from the longitudinal axis to an outer circumferential surface of the piston.

BRIEF DESCRIPTION OF THE DRAWINGS

FIG. 17 shows a side cross-sectional view of a dose divider along section line 17-17, according to an aspect of the disclosure.

FIG. 18 shows a side cross-sectional view of a dose divider along section line 18-18, according to an aspect of the disclosure.

DETAILED DESCRIPTION

Figure 1:
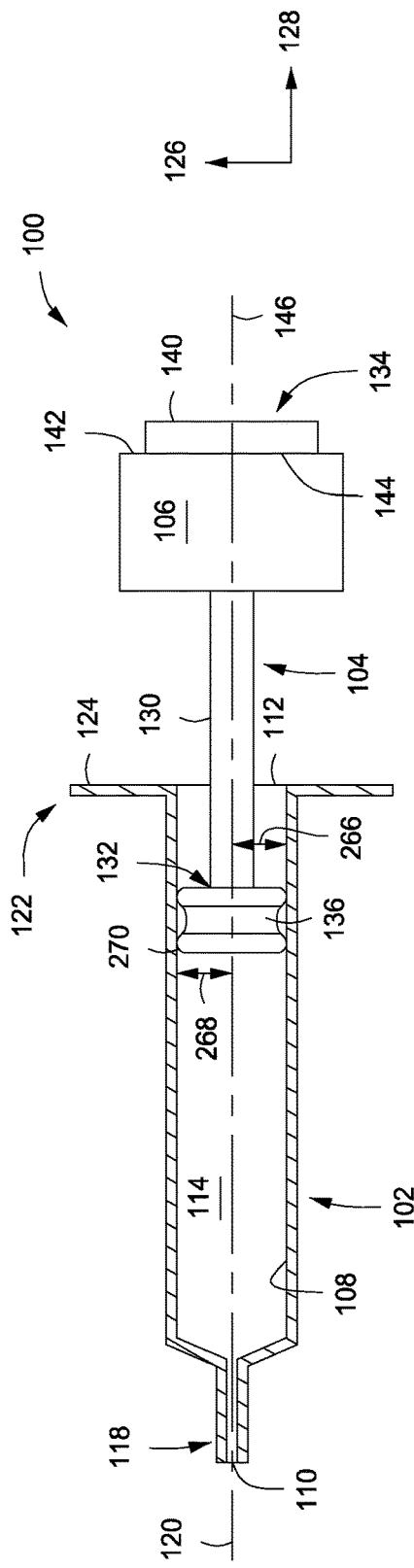
FIG. 1 is a schematic view of a syringe, according to an aspect of the disclosure.

Different aspects of the disclosure will now be described with reference to the drawing figures, in which like reference numerals refer to like parts throughout, unless otherwise specified.

FIG. 1 shows a schematic view of a syringe 100, according to an aspect of the disclosure. The syringe 100 includes a barrel 102, a plunger 104, and a dose divider 106. The barrel 102 has an internal surface 108 defining a first aperture or port 110, a second aperture or port 112, and an internal bore 114 extending therebetween. The first aperture 110 may be located at a distal end 118 of the barrel 102 along a longitudinal axis 120 of the barrel 102, and the second aperture 112 may be located at a proximal end 122 of the barrel 102 along the longitudinal axis 120 of the barrel 102. It will be appreciated that the first aperture 110 may be centered on the longitudinal axis 120 but need not be centered on the longitudinal axis 120 to be considered located at the distal end 118 of the barrel 102. Further, it will be appreciated that the second aperture 112 may be centered on the longitudinal axis 120 but need not be centered on the longitudinal axis 120 to be considered located at the proximal end 122 of the barrel 102.

The barrel 102 may include a flange 124 extending away from the barrel 102 at least partly in a radial direction 126, where the radial direction 126 is perpendicular to an axial direction 128. According to an aspect of the disclosure, the axial direction 128 is parallel to the longitudinal axis 120. According to another aspect of the disclosure, the flange 124 extends away from the barrel 102 in substantially the radial direction 126.

The plunger 104 includes a shaft 130 having a distal end 132 and a proximal end 134, a piston 136 coupled to the distal end 132 of the shaft 130, and a dose divider 106 disposed between the distal end 132 and the proximal end 134 of the shaft. The plunger 104 may further include a flange 140 disposed at the proximal end 134 of the shaft 130, where the flange 140 extends outward from the shaft 130 at least partly in the radial direction 126. According to an aspect of the disclosure, a proximal surface 142 of the dose divider 106 bears against a distal surface 144 of the flange 140. According to another aspect of the disclosure, the dose divider 106 defines the proximal end 134 of the shaft 130. It will be appreciated that the shaft 130 could have a circular cross section, a polygonal cross section, a rectangular cross section, a cruciform cross section, or any other shaft cross section known to persons having skill in the art.

The dose divider 106 may completely surround the shaft 130, or just partly surround the shaft 130. According to an aspect of the disclosure, the dose divider 106 is fixed to the shaft 130, such that the dose divider 106 is not free to translate relative to the shaft 130 along a longitudinal axis 146 of the shaft 130, and the dose divider 106 is not free to rotate relative to the shaft 130 about the longitudinal axis 146. According to another aspect of the disclosure, the dose divider 106 is free to translate along the longitudinal axis 146 of the shaft 130, but fixed in rotation relative to the shaft 130 about the longitudinal axis 146. According to yet another aspect of the disclosure, the dose divider 106 is free to rotate relative to the shaft 130 about the longitudinal axis 146, but fixed in translation relative to the shaft 130 along the longitudinal axis 146. According to still yet another aspect of the disclosure, the dose divider 106 is free to translate relative to the shaft 130 along the longitudinal axis 146, and free to rotate relative to the shaft 130 about the longitudinal axis 146.

The plunger 104 is configured to translate within the bore 114 of the barrel 102 along the axial direction 128. Further, the piston 136 is configured for sliding and sealing engagement with the internal surface 108 of the barrel 102. According to one aspect of the disclosure, the longitudinal axis 120 of the barrel 102 is substantially coaxial with the longitudinal axis 146 of the plunger 104. However, it will be appreciated that the longitudinal axis 120 of the barrel 102 need not be substantially coaxial with the longitudinal axis 146 of the plunger 104.

Translation of the piston 136 away from the first aperture 110 along the axial direction 128 may act to draw material from outside the barrel 102 into the internal bore 114 of the barrel 102 via the first aperture 110. Conversely, translation of the piston 136 toward the first aperture 110 along the axial direction 128 may act to expel material out of the internal bore 114 of the barrel 102 via the first aperture 110.

The dose divider 106 is configured to limit travel of the piston 136 toward the first aperture 110 by effecting axial interference between the plunger 104 and the barrel 102. Further, different orientations of the dose divider 106 relative to the barrel 102, the plunger 104, or both, may effect different states of axial interference between the plunger 104 and the barrel 102. Accordingly, different orientations of the dose divider 106 may limit different doses or quantities of material expelled from the internal bore 114 of the barrel 102 via the first aperture 110.

Figure 2:
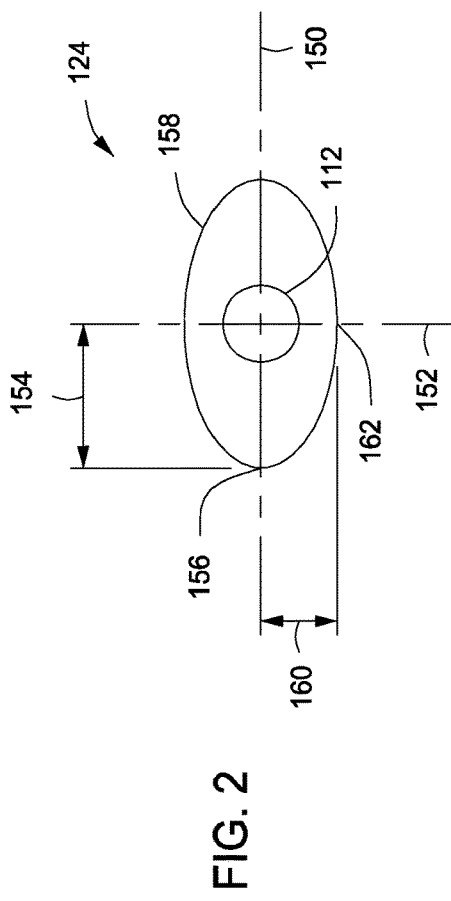
FIG. 2 is a plan view of a flange, according to an aspect of the disclosure.

FIG. 2 shows a plan view of the flange 124, looking along the axial direction 128, according to an aspect of the disclosure. The flange 124 may have a major axis 150 and a minor axis 152. Further, the major axis 150 and the minor axis 152 may intersect at substantially the longitudinal axis 120 of the barrel 102 (see FIG. 1). The flange 124 has a first radial dimension 154 from the minor axis 152 to a first point 156 on the periphery 158 of the flange 124, and a second radial dimension 160 from the major axis 150 to a second point 162 on the periphery 158 of the flange 124.

The periphery 158 of the flange 124 may be non-axisymmetric, such that the first radial dimension 154 is greater than the second radial dimension 160. According to an aspect of the disclosure, the first point 156 is defined by a point of intersection between the major axis 150 and the periphery 158 of the flange 124. According to another aspect of the disclosure, the second point 162 is defined by a point of intersection between the minor axis 152 and the periphery 158 of the flange 124.

It will be appreciated that the periphery 158 of the flange 124 could assume many different shapes such as, for example, an elliptical shape, a polygonal shape, a rectangular shape, an irregular shape, combinations thereof, or any other flange shape known to persons having skill in the art, and still include a major axis 150 and a minor axis 152. Further, it will be appreciated that the flange 140 of the plunger 104 may have structural attributes similar to those described for the flange 124 of the barrel 102. For example, according to an aspect of the disclosure, a periphery of the plunger flange 140 may have a non-axisymmetric shape and may have a major axis 150 and a minor axis 152.

Figure 3:
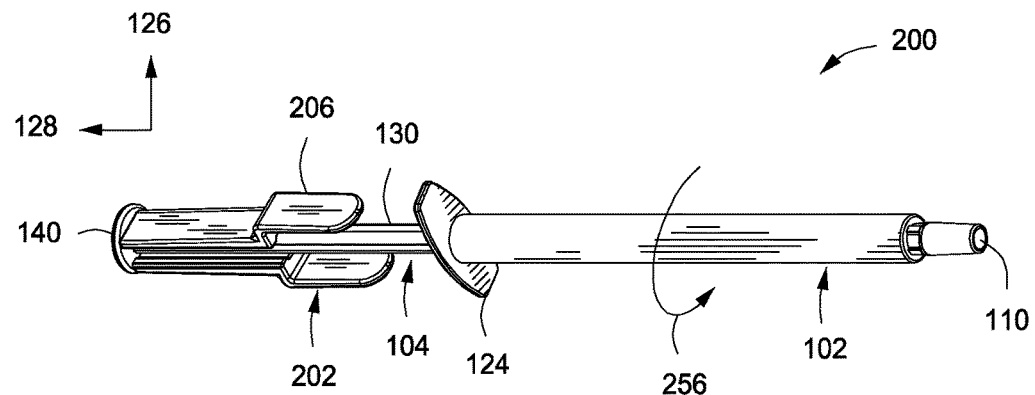
FIG. 3 is a perspective view of a syringe, according to an aspect of the disclosure.

FIG. 3 shows a perspective view of a syringe 200, according to an aspect of the disclosure. Similar to the syringe 100 shown in FIG. 1, the syringe 200 includes a barrel 102, a plunger 104 configured to translate within an internal bore 114 (see FIG. 1) of the barrel 102, and a dose divider 202 disposed along the shaft 130 of the plunger 104. According to an aspect of the disclosure, the dose divider 202 may be disposed at least partly around the shaft 130 of the plunger 104. The syringe 200 may further include a flange 124 extending from the barrel 102, a flange 140 extending from the plunger 104, or both.

Figure 4:
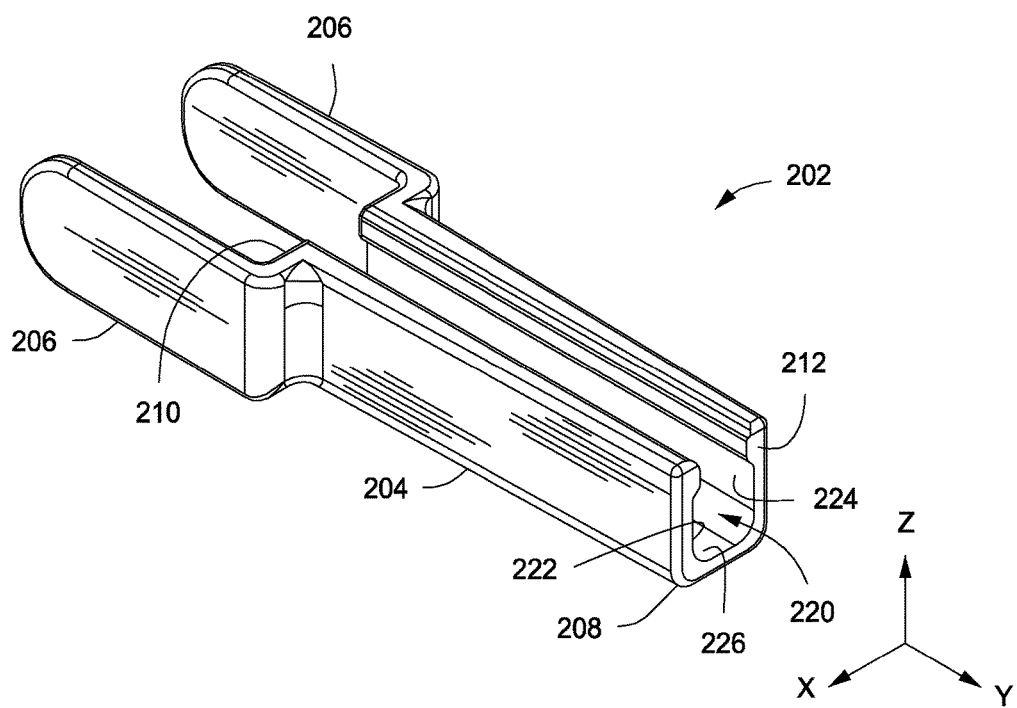
FIG. 4 is a perspective view of a dose divider, according to an aspect of the disclosure.
Figure 5:
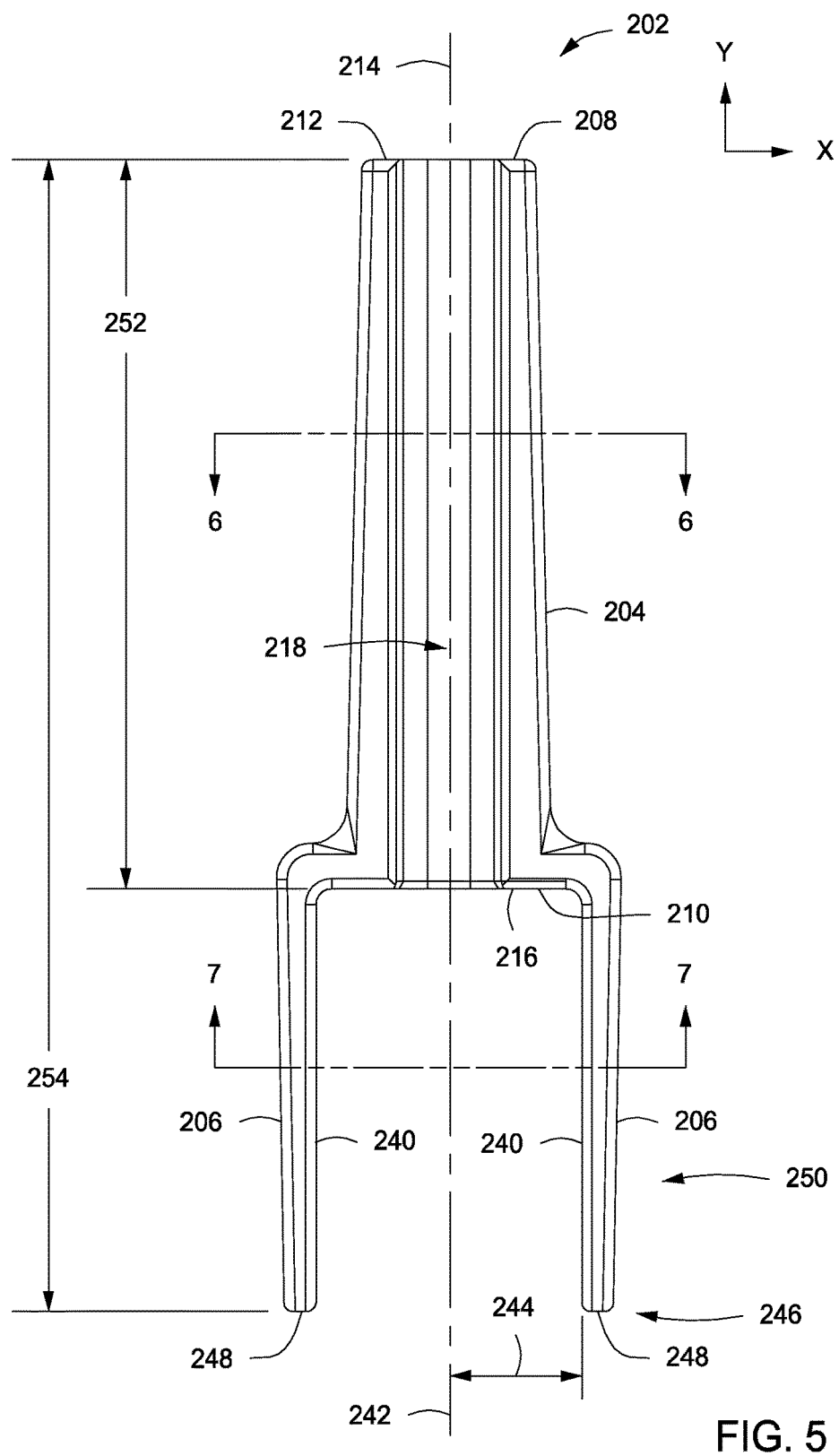
FIG. 5 is a front view of a dose divider, according to an aspect of the disclosure.
Figure 6:
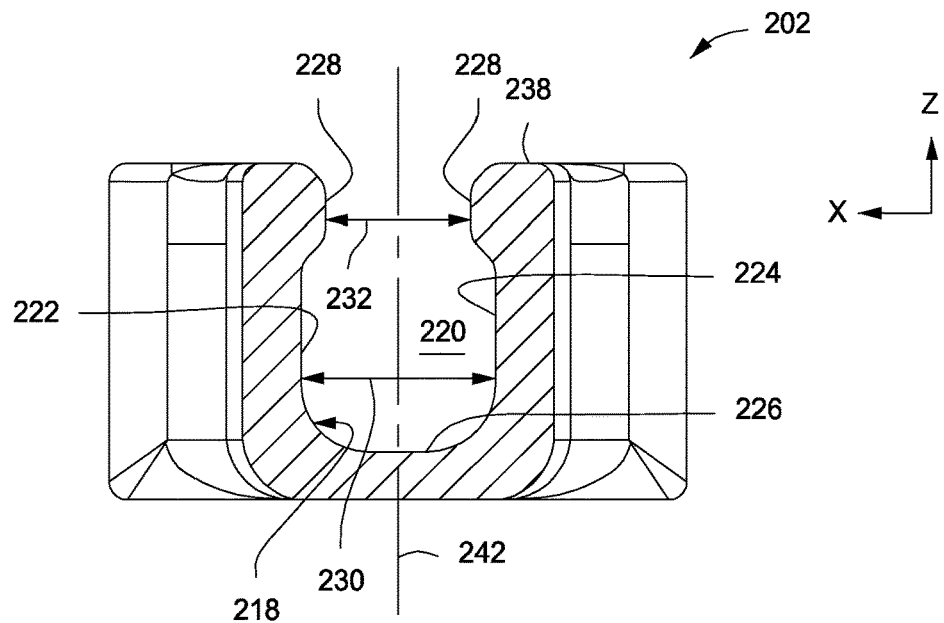
FIG. 6 is a side cross-sectional view of a dose divider along section line 6-6, according to an aspect of the disclosure.
Figure 7:
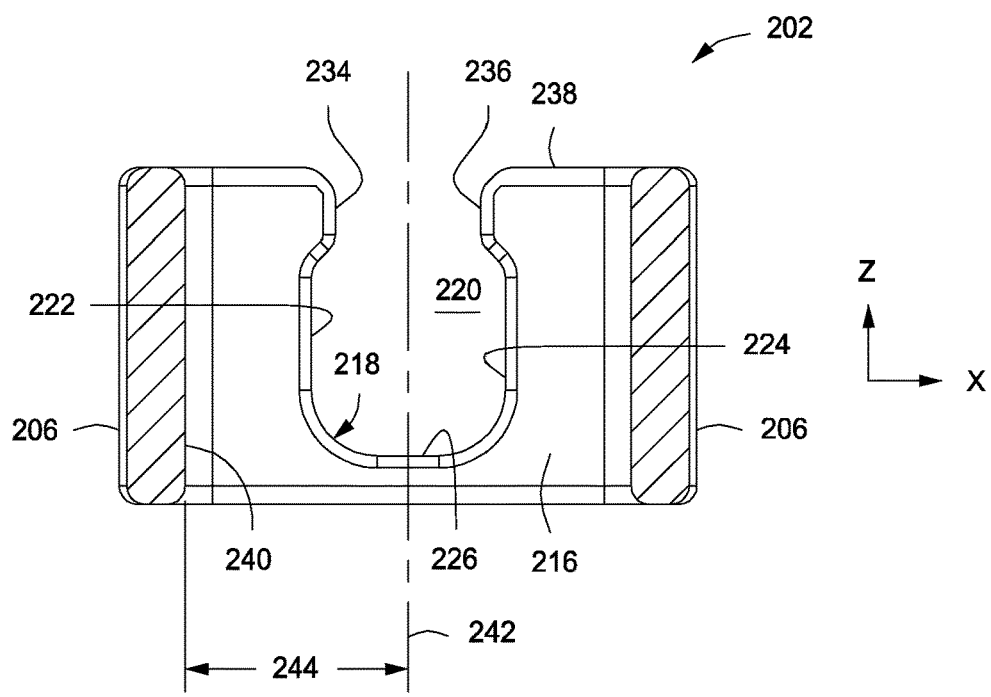
FIG. 7 is a side cross-sectional view of a dose divider along section line 7-7, according to an aspect of the disclosure.

Referring now to FIGS. 4-7, it will be appreciated that FIG. 4 shows a perspective view of the dose divider 202, according to an aspect of the disclosure; FIG. 5 shows a front view of the dose divider 202, according to an aspect of the disclosure; FIG. 6 shows a side cross sectional view of the dose divider 202 along section 6-6, according to an aspect of the disclosure; and FIG. 7 shows a side cross sectional view of the dose divider 202 along section 7-7, according to an aspect of the disclosure. The dose divider 202 includes a body 204 and at least one prong 206 extending away from the body 204.

As shown in FIG. 5, the body 204 extends from a proximal end 208 to a distal end 210. The proximal end 208 of the dose divider 202 includes a proximal surface 212 extending at least partially in the x-direction and the z-direction, where the x-direction is perpendicular to the longitudinal axis 214 of the dose divider 202, and the z-direction is perpendicular to both the x-direction and the longitudinal axis 214. The distal end 210 includes a first abutment surface 216 extending at least partially in the x-direction and the z-direction. Thus, the first abutment surface 216 at least partly faces the y-direction. According to one aspect of the disclosure, the proximal surface 212 extends substantially in a plane defined by the x-direction and the z-direction. According to another aspect of the disclosure, the first abutment surface 216 extends substantially in the plane defined by the x-direction and the z-direction.

The first abutment surface 216 may include a flat planar surface, a convex surface, or a concave surface. According to an aspect of the disclosure, the first abutment surface 216 is a substantially flat planar surface.

As shown in FIGS. 6 and 7, the body 204 includes an internal surface 218 defining a channel 220 extending along the longitudinal axis 214. The internal surface 218 may include a first wall 222 facing a second wall 224. Further, the internal surface 218 may include a third wall 226 extending between the first wall 222 and the second wall 224. According to an aspect of the disclosure, the first wall 222 and the second wall 224 lie substantially in a plane defined by the y-direction and the x-direction. According to another aspect of the disclosure, the third wall 226 extends substantially in a plane defined by the x-direction and the y-direction.

The internal surface 218 may also include one or more protuberances 228 that extend away from the first wall 222, the second wall 224, or both. The one or more protuberances 228 may extend in the z-direction from an upper surface 238 of the dose divider 202 toward the third wall 226. According to an aspect of the disclosure, a distance 230 along the x-direction from the first wall 222 to the second wall 224 is greater than a distance 232 along the x-direction from a protuberance 228 to a portion of the internal surface 218 facing the protuberance 228. According to another aspect of the disclosure, the one or more protuberances 228 includes a first protuberance 234 and a second protuberance 236.

The one or more protuberances 228 may each extend the entire axial length of the body 204. However, it will be appreciated that one or more of the protuberances 228 may extend less than the full axial length of the body 204. Further, the one or more protuberances 228 may include an array of protuberances arranged sequentially along the axial direction 128 on one or more sides of the internal surface 218.

According to an aspect of the disclosure, the distance 230 is greater than a circumscribed distance around the shaft 130 of the plunger 104 (see FIG. 3). According to another aspect of the disclosure, the distance 232 is less than a transverse distance across the shaft 130, such that the shaft 130, the dose divider 202, or both, may require elastic deformation to snap the shaft 130 into or out of the channel 220 of the dose divider 202 in the z-direction (see FIG. 3).

As shown in FIG. 5, the at least one prong 206 extends away from the distal end 210 of the dose divider 202 at least partly in the y-direction. According to an aspect of the disclosure, the prong 206 extends away from the distal end 210 of the dose divider 202 substantially in the y-direction.

A plane 242 extends in the z-direction and includes the longitudinal axis 214. An inner surface 240 of the at least one prong 206 may be spaced apart from a plane 242 in the x-direction by a distance 244. The distance 244 may be greater than or equal to the second radial dimension 160 of the flange 124 (see FIG. 2), and the distance 244 may be less than or equal to the first radial dimension 154 of the flange 124 (see FIG. 2).

According to an aspect of the disclosure, the distance 244 between the longitudinal axis 214 of the dose divider 202 and the inner surface 240 of the at least one prong 206 is greater than a radial distance 266 from the longitudinal axis 120 of the barrel 102 to the internal surface 108 of the barrel 102, measured near the proximal end 122 of the barrel 102 (see FIG. 1). According to another aspect of the disclosure, the distance 244 between the longitudinal axis 214 of the dose divider 202 and the inner surface 240 of the at least one prong 206 is greater than a radial distance 268 from the longitudinal axis 120 of the barrel 102 to an outer circumferential surface 270 of the piston 136 (see FIG. 1). The outer circumferential surface 270 of the piston 136 may be a sealing surface of the piston 136 configured for sliding and sealing engagement with the internal surface 108 of the barrel 102 (see FIG. 1).

The at least one prong 206 has a distal end 246 opposite the distal end 210 of the body 204, and the distal end 246 of the at least one prong 206 includes a second abutment surface 248 extending at least partly in the x-direction and the z-direction. Thus, the second abutment surface 248 at least partly faces the y-direction. The second abutment surface 248 may include a flat planar surface, a convex surface, or a concave surface. According to an aspect of the disclosure, the second abutment surface 248 is a convex surface. According to another aspect of the disclosure, the second abutment surface 248 is a flat planar surface.

The first abutment surface 216 may be spaced apart from the proximal surface 212 of the proximal end 208 of the dose divider 202 by a first axial distance 252. The second abutment surface 248 may be spaced apart from the proximal surface 212 of the proximal end of the dosed divider 202 by a second axial distance 254. According to an aspect of the disclosure, the second axial distance 254 is greater than the first axial distance 252.

Although FIGS. 3-5 show the dose divider 202 having two prongs 206, it will be understood that the at least one prong 206 may consist of only one prong 206. Further, it will be understood that if the at least one prong 206 includes a plurality of prongs 250, then each of the plurality of prongs 250 may have the same features attributed to the at least one prong 206.

Figure 8:
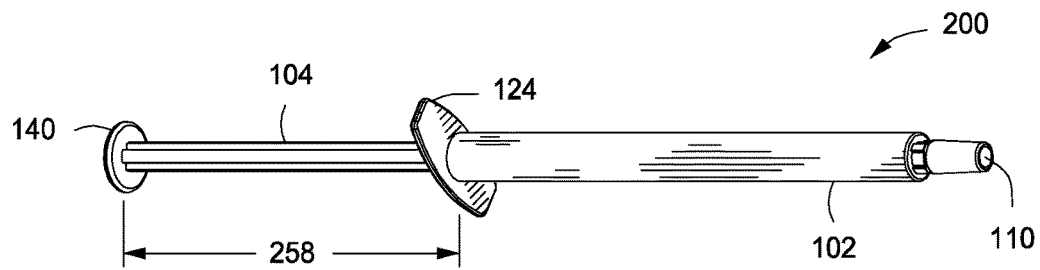
FIGS. 8-12 show perspective views of a syringe, according to various aspects of the disclosure.

Operation of the syringe 200 will now be described with reference to FIGS. 3 and 8-12, which show perspective views of the syringe 200, according to various aspects of the disclosure. FIG. 8 shows the syringe 200 with the dose divider 202 removed and the plunger 104 in a first axial location 258 with respect to the barrel 102. FIG. 8 may be representative of a configuration of the syringe 200 after a user translates the plunger 104 away from the barrel 102 in order to draw a material into the bore 114 (see FIG. 1) of the barrel 102.

Next, as shown in FIG. 3, a user may install the dose divider 202 onto the syringe 200 and orient the dose divider 202 in a first circumferential position with respect to the circumferential or azimuthal direction 256, such that the at least one prong 206 of the dose divider is configured to axially interfere with the flange 124. The at least one prong 206 may be substantially aligned with a major axis 150 (see FIG. 2) of the flange 124, thereby configuring the at least one prong 206 of the dose divider 202 to axially interfere with the flange 124. However, it will be appreciated that the first circumferential position of the at least one prong 206 relative to the barrel 102 could be any circumferential position that enables axial interference between the at least one prong 206 and the flange 124. FIG. 3 may be representative of a configuration of the syringe 200 after filling the barrel 102 with a material and before expelling air, a first portion of material, or both, from the first aperture 110 of the barrel to set a cumulative dose quantity of material within the syringe 200.

Figure 9:
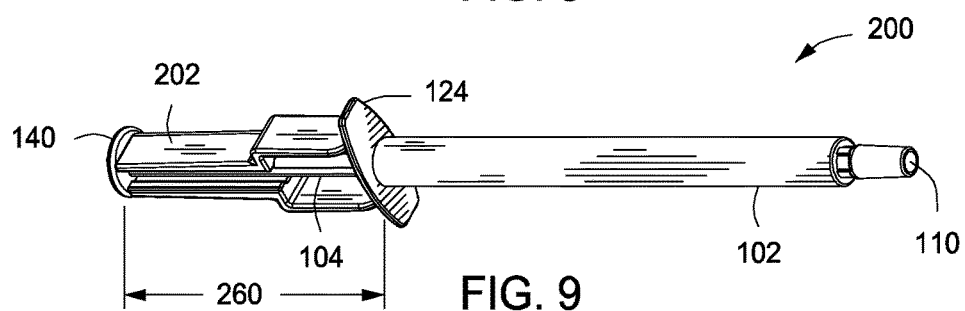

Then, the plunger 104 is translated toward the barrel 102 until the plunger 104 is located in a second axial position 260 with respect to the barrel 102, where the at least one prong 206 bears on the flange 124, as shown in FIG. 9. According to an aspect of the disclosure, the second abutment surface 248 (see FIG. 5) of the at least one prong 206 bears on the flange 124 when the plunger 104 is located in the second axial position relative to the barrel 102. Thus, FIG. 9 may be representative of a configuration of the syringe 200 after setting a cumulative dose quantity of material within the syringe 200 but before delivering any dose of material to a patient.

Figure 10:
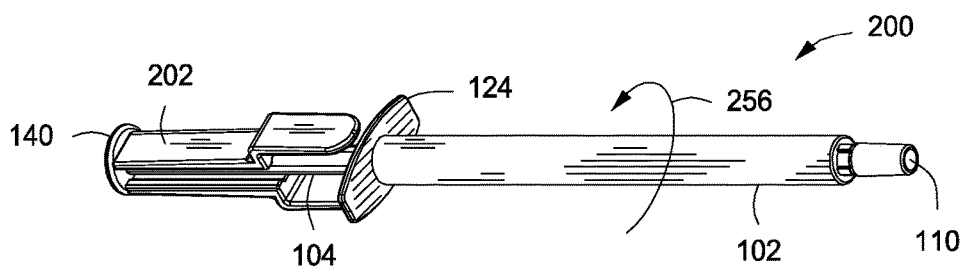

Next, the dose divider 202 is rotated relative to the barrel 102 in the circumferential direction 256 from the first circumferential position to a second circumferential position, such that the at least one prong 206 is configured to not interfere axially with the flange 124, as shown in FIG. 10. The at least one prong 206 may be substantially aligned with the minor axis 152 (see FIG. 2) of the flange 124, thereby configuring the at least one prong 206 of the dose divider 202 to be free from axial interference with the flange 124. However, it will be appreciated that the second circumferential position of the dose divider 202 with respect to the flange 124 could be any relative circumferential location that avoids axial interference between the at least one prong 206 and the flange 124. Further according to the second circumferential location of the dose divider 202 relative to the flange 124, the second abutment surface 248 may be circumferentially aligned with the flange 124 to enable axial interference therewith. Thus, FIG. 10 may be representative of a configuration of the syringe 200 just before delivering a second portion of material, or a first dose of material, out of the first aperture 110 of the syringe 200.

Figure 11:
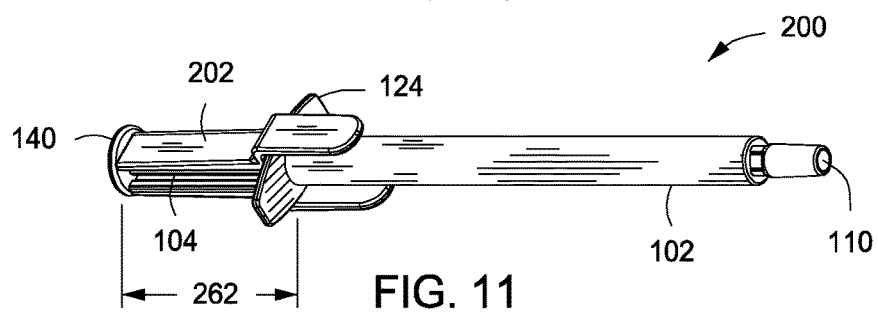

Then, the plunger 104 may be translated toward the barrel 102 from the second axial position 260 to a third position 262 relative to the barrel, such that the first abutment surface 216 bears on the flange 124, as shown in FIG. 11. Accordingly, by translating the plunger 104 toward the barrel 102 from the second axial position 260 to the third axial position 262, a second portion of material may be delivered out of the first aperture 110 of the barrel. According to an aspect of the disclosure, the second portion of material is a first dose of material delivered to a patient via the first aperture 110 of the syringe 200.

Figure 12:
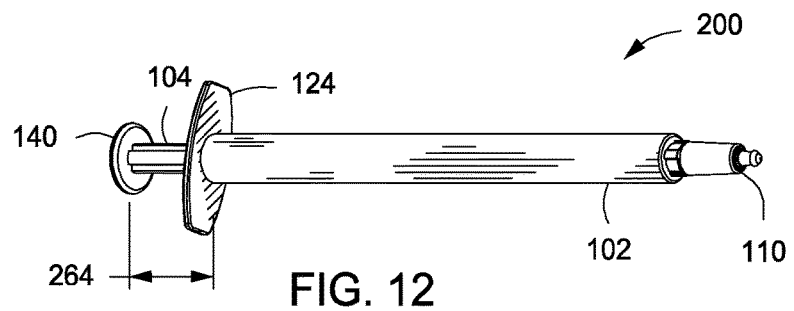

Next, the dose divider 202 may be removed from the syringe 200, and the plunger 104 may be translated toward the barrel 102 from the third axial position 262 to a fourth axial position 264 relative to the barrel 102, as shown in FIG. 12. Accordingly, by translating the plunger 104 toward the barrel 102 from the third axial position 262 to the fourth axial position 264, a third portion of material may be delivered out of the first aperture 110 of the barrel. According to an aspect of the disclosure, the third portion of material is a second dose of material delivered to a patient via the first aperture 110 of the syringe 200.

Although FIGS. 3 and 8-12 show the dose divider 202 arranged on the syringe 200 such that the first abutment surface 216 and the second abutment surface 248 face the flange 124 of the barrel 102, it will be appreciated that the syringe 200 could be similarly operated with the dose divider 202 arranged such that the first abutment surface 216 and the second abutment 248 surface face the flange 140 of the plunger 104.

Figure 13:
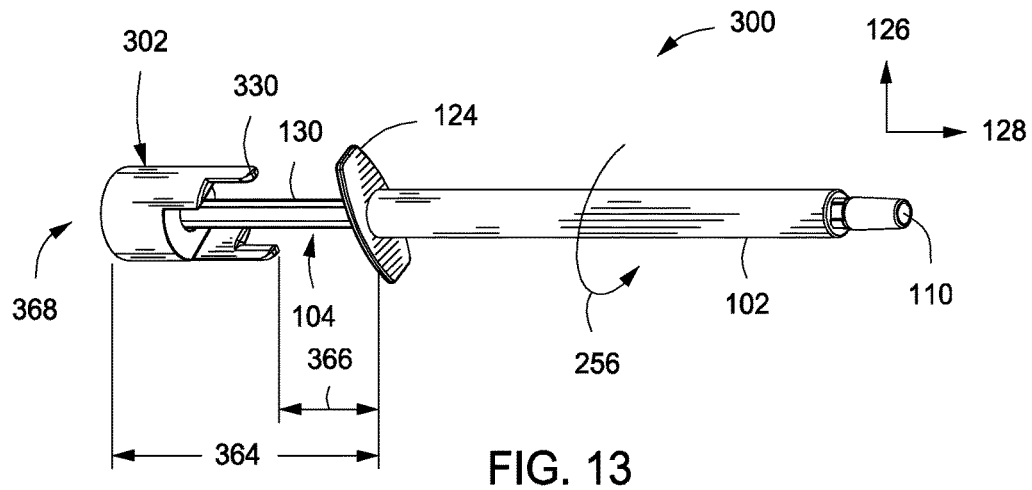
FIG. 13 shows a perspective view of a syringe, according to an aspect of the disclosure.

FIG. 13 shows a perspective view of a syringe 300, according to an aspect of the disclosure. Similar to the syringe 100 shown in FIG. 1, the syringe 300 includes a barrel 102, a plunger 104 configured to translate within an internal bore 114 (see FIG. 1) of the barrel 102, and a dose divider 302 disposed along the shaft 130 of the plunger 104. According to an aspect of the disclosure, the dose divider 302 may be disposed at least partly around the shaft 130 of the plunger 104. The syringe 300 may further include a flange 124 extending from the barrel 102, a flange 140 extending from the plunger 104, or both.

Figure 14:
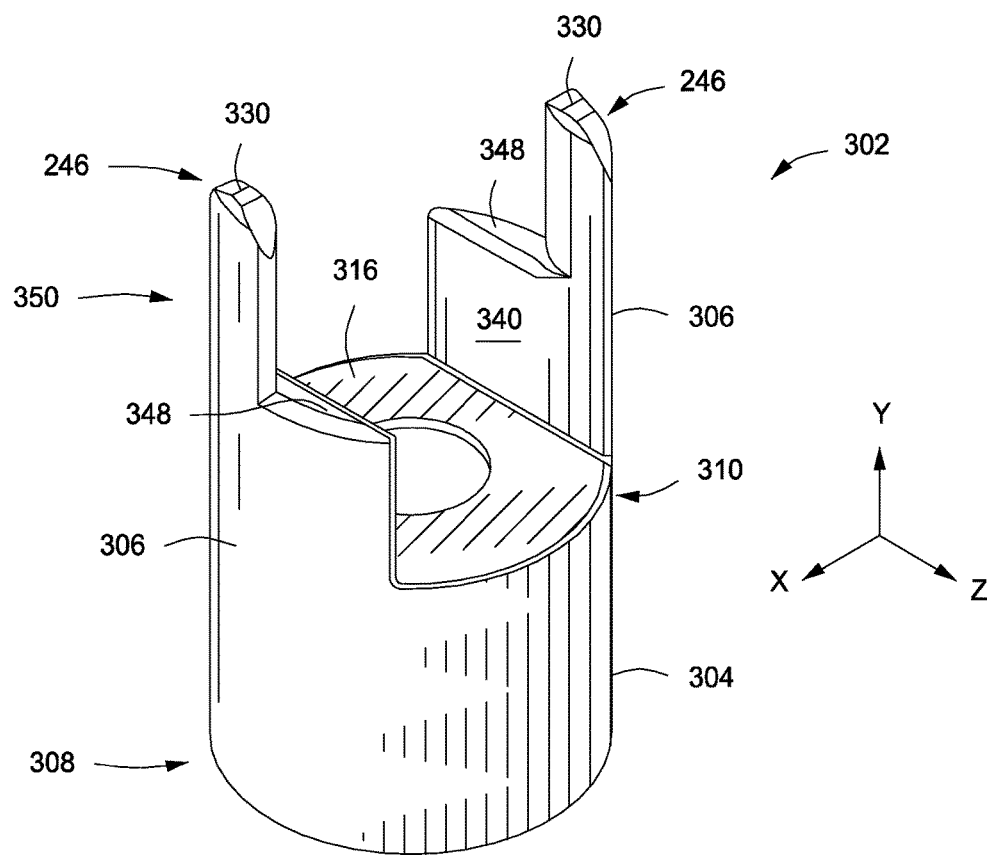
FIG. 14 shows a perspective view of a dose divider, according to an aspect of the disclosure.
Figure 15:
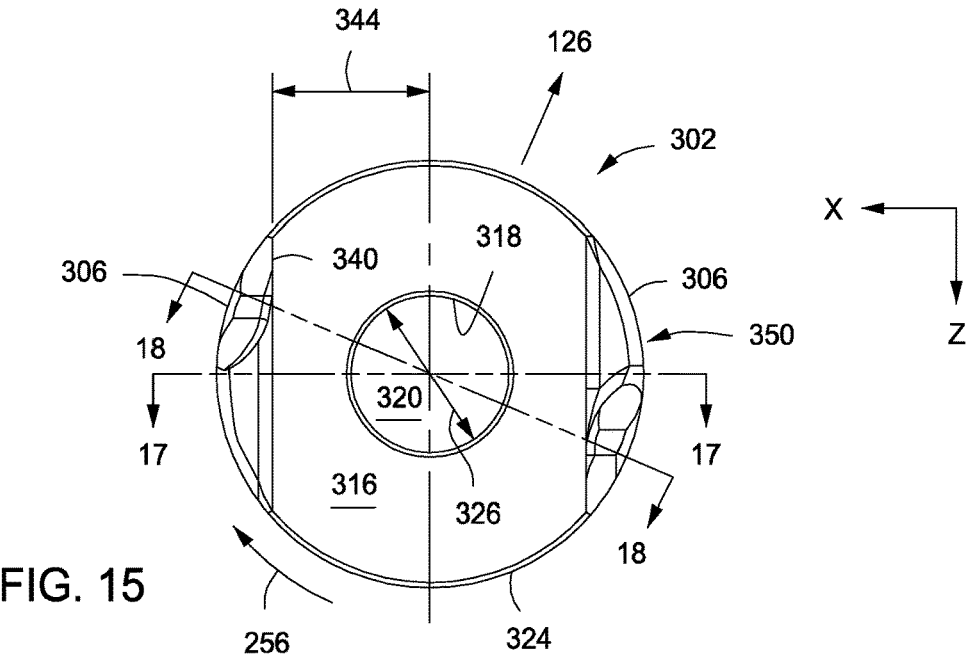
FIG. 15 shows a top view of a dose divider, according to an aspect of the disclosure.
Figure 16:
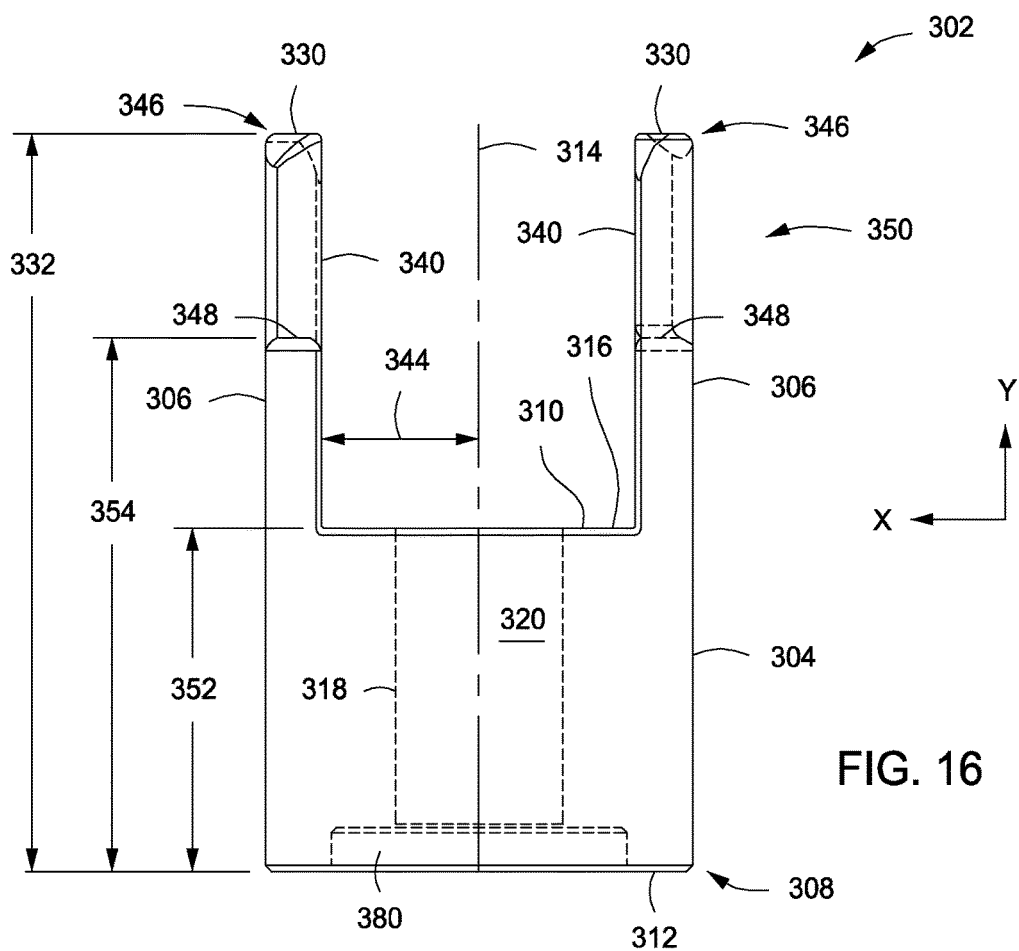
FIG. 16 shows a side view of a dose divider, according to an aspect of the disclosure.

Referring to FIGS. 14-18, it will be appreciated that FIG. 14 shows a perspective view of the dose divider 302, according to an aspect of the disclosure; FIG. 15 shows a top view of the dose divider 302, according to an aspect of the disclosure; FIG. 16 shows a front view of the dose divider 302, according to an aspect of the disclosure; FIG. 17 shows a front cross sectional view of the dose divider 302 along section 17-17, according to an aspect of the disclosure; and FIG. 18 shows a front cross sectional view of the dose divider 302 along section 18-18, according to an aspect of the disclosure. The dose divider 302 includes a body 304 and at least one prong 306 extending away from the body 304.

As shown in FIGS. 16-18, the body 304 extends from a proximal end 308 to a distal end 310. The proximal end 308 of the dose divider 302 includes a proximal surface 312 extending at least partially in the x-direction and the z-direction, where the x-direction is perpendicular to the longitudinal axis 314 of the dose divider 302, and the z-direction is perpendicular to both the x-direction and the longitudinal axis 314. The distal end 310 includes a first abutment surface 310 extending at least partially in the x-direction and the z-direction. Thus, the first abutment surface 316 at least partly faces the y-direction. According to one aspect of the disclosure, the proximal surface 312 extends substantially in a plane defined by the x-direction and the z-direction. According to another aspect of the disclosure, the first abutment surface 316 extends substantially in the plane defined by the x-direction and the z-direction.

As shown in FIGS. 15-18, the body 304 includes an internal surface 318 defining a bore or channel 320 extending along the longitudinal axis 314. The internal surface 318 may completely surround the bore 320 about a circumferential direction 256. Alternatively, the internal surface 318 may extend at least partly in a radial direction 126 to intersect with an external surface 324 of the dose divider 302, thereby forming an open channel 320 similar to channel 220 (see FIG. 4). The bore 320 may have a circular cross section, a polygonal cross section, a square cross section, and elliptical cross section, or any other bore or channel cross section known to persons having ordinary skill in the art.

The bore or channel 320 may be configured to receive the shaft 130 of the plunger 104 in sliding engagement. According to an aspect of the disclosure, an internal dimension 326 of the bore 320 may be greater than a circumscribed dimension about the shaft 130 of the plunger 104 (see FIG. 1). Alternatively, the dose divider 302 may be formed integrally with the shaft 130 of the plunger 104 (see FIG. 1), or the shaft 130 of the plunger 104 may have an interference fit with the bore or channel 320 of the dose divider 302, such that the dose divider 302 moves in rigid body translation, rigid body rotation, or both, with the shaft 130 of the plunger 104.

As shown in FIG. 16, the at least one prong 306 extends away from the distal end 310 of the dose divider 302 at least partly in the y-direction. According to an aspect of the disclosure, the prong 306 extends away from the distal end 310 of the dose divider 302 substantially in the y-direction.

An inner surface 340 of the at least one prong 306 may be spaced apart from the longitudinal axis 314 by a distance 344. According to an aspect of the disclosure, the distance 344 is measured perpendicular to the inner surface 340. The distance 344 may be greater than or equal to the second radial dimension 160 of the flange 124 (see FIG. 2), and the distance 344 may be less than or equal to the first radial dimension 154 of the flange 124 (see FIG. 2).

According to an aspect of the disclosure, the distance 344 between the longitudinal axis 314 of the dose divider 302 and the inner surface 340 of the at least one prong 306 is greater than a radial distance 266 from the longitudinal axis 120 of the barrel 102 to the internal surface 108 of the barrel 102, measured near the proximal end 122 of the barrel 102 (see FIG. 1). According to another aspect of the disclosure, the distance 344 between the longitudinal axis 314 of the dose divider 302 and the inner surface 340 of the at least one prong 306 is greater than a radial distance 268 from the longitudinal axis 120 of the barrel 102 to an outer circumferential surface 270 of the piston 136 (see FIG. 1).

The at least one prong 306 has a distal end 346 opposite the distal end 310 of the body 304, and the distal end 346 of the at least one prong 306 includes a second abutment surface 348, and a third abutment surface 330, each extending at least partly in the x-direction and the z-direction. Thus, the second abutment surface 348 and the third abutment surface 330 each at least partly faces the y-direction. Either the second abutment surface 348 or the third abutment surface 330 may include a flat planar surface, a convex surface, or a concave surface. According to an aspect of the disclosure, the second abutment surface 348 is a planar surface. According to another aspect of the disclosure, the third abutment surface 330 is a convex surface.

The first abutment surface 316 may be spaced apart from the proximal surface 312 of the proximal end 308 of the dose divider 302 by a first axial distance 352. The second abutment surface 348 may be spaced apart from the proximal surface 312 of the proximal end 308 of the dose divider 302 by a second axial distance 354. The third abutment surface 330 may be spaced apart from the proximal surface 312 of the proximal end 308 of the dose divider 302 by a third axial distance 332. According to an aspect of the disclosure, the second axial distance 254 is greater than the first axial distance 252. According to another aspect of the disclosure, the third axial distance 332 is greater than the second axial distance 254.

Although FIGS. 13-18 show the dose divider 302 having two prongs 306, it will be understood that the at least one prong 306 may consist of only one prong 306. Further, it will be understood that if the at least one prong 306 includes a plurality of prongs 350, then each of the plurality of prongs 350 may have the same features attributed to the at least one prong 306.

The plurality of prongs 350 may include a pair of prongs 306 located at circumferential locations about the dose divider 302 that diametrically face one another with respect to the longitudinal axis 314. According to an aspect of the disclosure, the pair of prongs 306 may include a pair of second abutment surfaces 348 located at circumferential locations about the dose divider 302 that diametrically face one another with respect to the longitudinal axis 314. According to another aspect of the disclosure, the pair of prongs 306 may include a pair of third abutment surfaces 330 located at circumferential locations about the dose divider 302 that diametrically face one another with respect to the longitudinal axis 314.

Referring to FIGS. 16-18, the internal surface 318 may define a counter sink 380 disposed in a proximal end 308 of the dose divider 302. The counter sink 380 may have a cross section in the x-z plane having a circular shape, a polygonal shape, a rectangular shape, a square shape, a triangular shape, a hexagonal shape, an oval shape, combinations thereof, or any other counter sink cross sectional shape known to persons having skill in the art. According to an aspect of the disclosure, the counter sink 380 is configured to receive the flange 140 of the plunger 104 therein. According to another aspect of the disclosure, the flange 140 interferes with counter sink 380 in a rotational direction about the longitudinal axis 146, such that the flange 140 may transmit a torque to the dose divider 302 via the counter sink 380, or vice versa. According to yet another aspect of the disclosure, the flange 140 is free from rotational interference with the counter sink 380.

Figure 19:
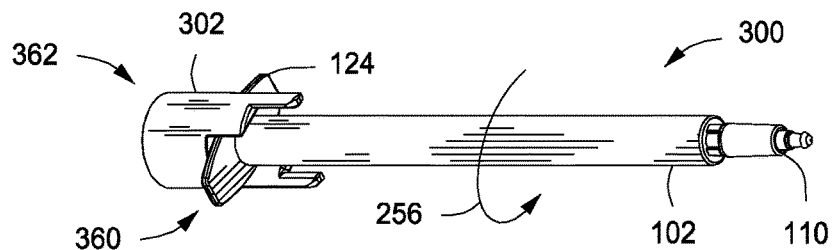
FIGS. 19-23 show perspective views of a syringes according to various aspects of the disclosure.

Operation of the syringe 300 will now be described with reference to FIGS. 13 and 19-23, which show perspective views of the syringe 300, according to various aspects of the disclosure. FIG. 19 shows the syringe 300 with the plunger 104 located in a first axial position 360 relative to the barrel 102, such that the plunger 104 is in a location of maximum translation toward the first aperture 110 of the barrel 102. In the first axial position 360, the plunger 104 may bear axially on the internal surface 108 (see FIG. 1) of the barrel 102, the dose divider 302 may bear on the flange 124, or both the dose divider 302 and the plunger 104 may bear axially on the barrel 102. According to an aspect of the disclosure, the first abutment surface 316 of the dose divider 302 bears on the flange 124 of the barrel 102 when the plunger 104 is located in the first axial position 360 relative to the barrel 102.

Further according to FIG. 19, the dose divider 302 is located in a first circumferential location 362 relative to the barrel 102 about the circumferential or azimuthal direction 256. In the first circumferential location 362, the second abutment surface 348 and the third abutment surface 330 of at least one prong 306 may be free from axial interference with the flange 124. Accordingly, FIG. 19 may be representative of a configuration of the syringe 300 as received by a user, before filling the syringe 300 with a material.

Next, as shown in FIG. 13, the plunger 104 may be translated away from the first aperture 110 from the first axial position 360 to a second axial position 364. According to an aspect of the disclosure, the second axial position 364 of the plunger 104 effects an axial gap 366 between the third abutment surface 330 and the flange 124. It will be appreciated that translation of the plunger 104 relative to the barrel 102 from the first axial position 360 to the second axial position 364 could be used to fill the syringe 300 with a material to be dispensed.

Further according to FIG. 13, the dose divider 302 is rotated relative to the barrel 102 from the first circumferential location 362 to a second circumferential location 368. According to an aspect of the disclosure, the dose divider 302 may be configured to enable axial interference between the third abutment surface 330 and the flange 124 when the dose divider 302 is rotated to the second circumferential location 368. According to another aspect of the disclosure, the third abutment surface 330 is rotationally aligned with the major axis 150 of the flange 124 (see FIG. 2) when the dose divider 302 is rotated to the second circumferential location 368. Thus, FIG. 13 may be representative of a configuration of the syringe 300 after filling the syringe 300 with a material but before dispensing any portion of the material out of the first aperture 110.

Figure 20:
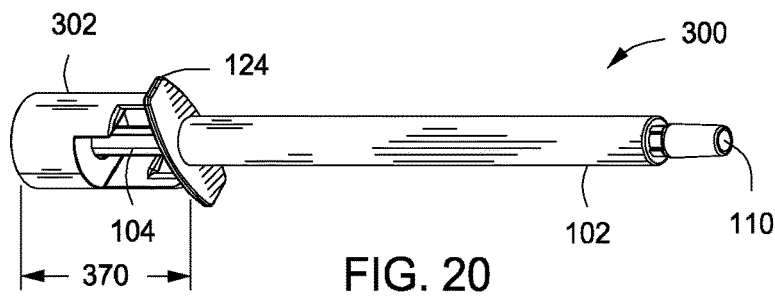

Then, the plunger 104 is translated toward the barrel 102 until the plunger 104 is located in a third axial position 370 with respect to the barrel 102, as shown in FIG. 20. According to an aspect of the disclosure, the third abutment surface 330 (sea FIG. 14) of the at least one prong 306 bears on the flange 124 when the plunger 104 is located in the third axial positron 170 relative to the barrel 102. According to another aspect of the disclosure, the second abutment surface 348 does not bear on the flange 124 when the plunger 104 is located in the third axial position 170 relative to the barrel 102.

It will be appreciated that translating the plunger from the second axial position 364 to the third axial position 320 may act to expel air, a first portion of material, or both, from the first aperture 110 of the syringe 300, thereby setting a cumulative dose quantity of material within the syringe 300. Thus, FIG. 20 may be representative of a configuration of the syringe 300 after setting a cumulative dose quantity of material within the syringe 200 but before delivering any dose of material to a patient.

Figure 21:
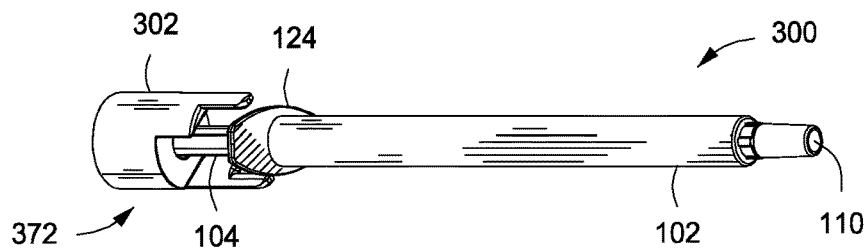

Next, the dose divider 302 is rotated relative to the barrel 102 in the circumferential direction 256 from the second circumferential location 368 to a third circumferential location 372, such that the third abutment surface 330 is arranged to not interfere axially with the flange 124, and the second abutment surface 348 is arranged to axially interfere with the flange 124, as shown in FIG. 21. Thus, FIG. 21 may be representative of a configuration of the syringe 300 just before delivering a second portion of material out of the first aperture 110.

Figure 22:
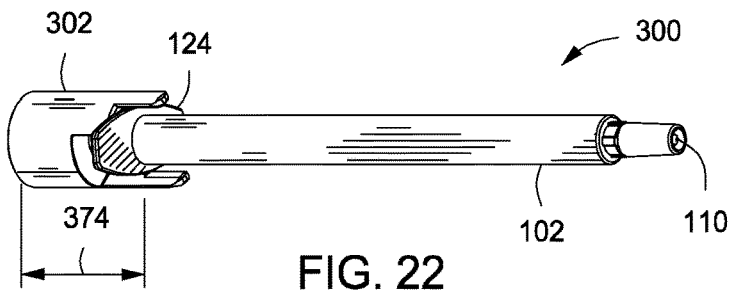

Then, the plunger 104 may be translated toward the barrel 102 from the third axial position 370 to a fourth axial position 374 relative to the barrel 102, such that the second abutment surface 348 bears on the flange 124, as shown in FIG. 22. Accordingly, between the configurations of the syringe 200 shown in FIGS. 21 and 22, a second portion of material may be delivered out of the first aperture 110 of the barrel 102. According to an aspect of the disclosure, the second portion of material is a first dose of material delivered to a patient via the first aperture 110 of the syringe 200.

Figure 23:
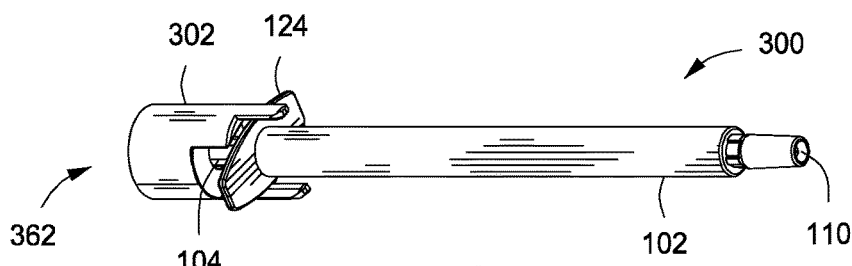

Next, the dose divider 302 is rotated relative to the barrel 102 in the circumferential direction 256 from the third circumferential location 372 to the first circumferential location 362, such that neither the second abutment surface 348 nor the third abutment surface 330 is arranged to axially interfere with the flange 124, and so that the first abutment surface 316 is arranged to axially interfere with the flange 124, as shown in FIG. 23. Thus, FIG. 23 may be representative of a configuration of the syringe 300 just before delivering a third portion of material out of the first aperture 110.

Then, the plunger 104 may be translated toward the barrel 102 from the fourth axial position 374 to a fifth axial position 376 relative to the barrel 102, thereby delivering a third portion of material out of the first aperture 110 of the barrel 102. According to an aspect of the disclosure, the third portion of material is a second dose of material delivered to a patient via the first aperture 110 of the syringe 200. According to another aspect of the disclosure, the fifth axial position 376 is the same as the first axial position 360, shown in FIG. 19.

Although FIGS. 13 and 19-23 show the dose divider 302 arranged on the syringe 300 such that the first abutment surface 316, the second abutment surface 348 and the third abutment surface 330 face the flange 124 of the barrel 102, it will be appreciated that the syringe 300 could be similarly operated with the dose divider 302 arranged such that the first abutment surface 316, the second abutment surface 348 and the third abutment surface 330 face the flange 140 of the plunger 104.

The present disclosure is applicable to syringes in general, and more particularly, to syringes that provide tactile feedback of material quantity delivered to the user. Further, the present disclosure may be applicable to syringes used in the context of medicine, manufacturing, construction, maintenance and repair, agriculture, food preparation, or any other context where syringes may be used. Accordingly, aspects of the disclosure may be applied to syringes for delivering a medication to a patient, extracting bodily fluids from a patient, or delivering other fluid materials such as air, adhesives, lubricants, food products, and the like.

Applicants have identified a need for delivering multiple doses of medication from a single syringe using rapid plunger motion to deliver each of the multiple doses. For example, nasal administration of medications may benefit from delivery of partial doses to each nostril of a patient in quick succession and with a high degree of atomization.

The degree of atomization increases with increasing pressure drop across the atomization orifice, and therefore, increasing flow rate through the atomization orifice. Accordingly, the degree of atomization may benefit from higher velocities of the plunger 104 relative to the barrel 102 during medicine delivery. In turn, Applicants have identified that high plunger velocities for multi-dose syringes may result in repeatability and reproducibility errors, in both the amount of medicine in each dose and the degree of atomization, when dose quantity is controlled via visual feedback of a relative position of the plunger 104 within the barrel 102 of the syringe. Indeed, errors in dose quantity based on visual feedback may be exacerbated by the need for high plunger velocities at least because of difficulty in rapidly decelerating the plunger 104 to while simultaneously stopping precisely at the axial location corresponding to a desired dose.

Aspects of the disclosure address drawbacks of conventional approaches by providing tactile dose feedback through variable interference between the plunger 104 and the barrel 102 of a syringe, instead of conventional visual feedback. As described previously, the orientation of a dose divider 106, 202, 302 relative to the barrel 102, the plunger 104, or both, may be varied according to aspects of the disclosure to provide variable degrees of tactile interference between the plunger 104 and the barrel 102 via the dose divider 106, 202, 302. Indeed, by providing variable degrees of interference between the plunger 104 and the barrel 102 via the dose divider 106, 202, 302 to limit the individual dose quantities, syringe users may allocate more attention to the rate of plunger travel and the location of the aperture 110 relative to a patient's nose, thereby improving repeatability and reproducibility of both dose quantity and the degree of atomization.

Further, aspects of the disclosure provide dose dividers 106, 202, 302 that are reusable. For example, the dose divider 202 shown in FIGS. 3-5 may be removable from the shaft 130 of the plunger 104 (see FIG. 1), and does not necessarily come in contact with either the medicine dispensed or the patient, thereby allowing the dose divider 202 to be used with more than one syringe. Further, a kit of multiple dose dividers 202, each having different distances between the respective abutment surfaces, may be employed in combination with a single syringe design to deliver a variety of dose quantity schedules. The individual dose dividers 202, for example, could be distinguished from one another by color, numerical indicia, alphabetical indicia, or other distinguishing feature known to persons with ordinary skill in the art.

In addition, aspects of the disclosure provide dose dividers 106, 202, 302 that do not impede translation of the plunger 104 away from the barrel 102, for example during filling procedures. Unlike conventional multiple-dose syringes, such as those described in the '544 patent and the '467 publication, discussed above, syringes according to the present disclosure may not require rotation of the plunger shaft 130 in order to fill the syringes with material.

The syringe 200, 300 may be configured such that the first dose of material may be substantially equal in quantity to the second dose of material. However, it will be appreciated that the syringe 200 may also be configured such that the quantity of the first dose of material is different from the quantity of the second dose of material for other material delivery processes.

Unless specified otherwise herein, the word "substantially" shall mean "considerable in extent," or shall mean largely but not necessarily wholly that which is specified.

It will be appreciated that the foregoing description provides examples of the disclosed apparatus and method. However, it is contemplated that other implementations of the disclosure may differ in detail from the foregoing examples. All references to the disclosure or examples thereof are intended to reference the particular example being discussed at that point and are not intended to imply any limitation as to the scope of the disclosure more generally. All language of distinction and disparagement with respect to certain features is intended to indicate a lack of preference for those features, but not to exclude such from the scope of the disclosure entirely unless otherwise indicated.

Recitation of ranges of values herein are merely intended to serve as a shortband method of referring individually to each separate value falling with the range, unless otherwise indicated herein, and each separate value is incorporated into the specification as if it were individually recited herein. All methods described herein can be performed in any suitable order unless otherwise indicated herein or otherwise clearly contradicted by context.

We claim:

1. A syringe, comprising: a barrel having an internal surface defining an internal bore therein, the barrel further comprising a flange disposed near a proximal end of the barrel; a plunger disposed within the internal bore of the barrel, the plunger having a shaft having a longitudinal axis; a dose divider disposed on the plunger, the dose divider being rotatable about the longitudinal axis of the plunger, the dose divider including a first end, a first abutment surface facing an axial direction along the longitudinal axis of the plunger, the first abutment surface being spaced apart from the first end in the axial direction by a first axial distance, wherein the first abutment surface is configured to bear on the flange of the barrel when the plunger is in a first axial position relative to the barrel, and a second abutment surface facing the axial direction, the second abutment surface being spaced apart from the first end in the axial direction by a second axial distance, the second axial distance being greater than the first axial distance, the second abutment surface being spaced apart from the longitudinal axis of the plunger by a first radial distance, wherein the second abutment surface is configured to bear on the flange of the barrel when the plunger is in a second axial position relative to the barrel, the second axial position being different from the first axial position, wherein the dose divider further includes a third abutment surface facing the axial direction, the third abutment surface being spaced apart from the first end in the axial direction by a third axial distance, the third axial distance being greater than the second axial distance, the third abutment surface being spaced apart from the longitudinal axis of the plunger by a second radial distance, wherein the third abutment surface is configured to bear on the flange of the barrel when the plunger is in a third axial position relative to the barrel, the third axial position being different from the first axial position and the second axial position wherein the first radial distance and the second radial distance are greater than a radial distance from a longitudinal axis of the barrel to the internal surface of the barrel in which the plunger is disposed and which is distal to the flange.

2. The syringe according to claim 1, the flange extending from the barrel in a radial direction, the radial direction being normal to a longitudinal axis of the barrel,
wherein the flange has a first radial dimension from the longitudinal axis to a first point on a periphery of the flange, and a second radial dimension from the longitudinal axis to a second point on the periphery of the flange, the first radial dimension being greater than the second radial dimension, and
wherein the first radial distance of the dose divider is less than the first radial dimension of the flange and greater than the second radial dimension of the flange.

3. The syringe according to claim 1, wherein the second radial distance is approximately equal to the first radial distance.

4. The syringe according to claim 1, wherein the dose divider further includes a fourth abutment surface facing the axial direction, the fourth abutment surface being spaced apart from the first end in the axial direction by the third axial distance, the fourth abutment surface being spaced apart from the longitudinal axis of the plunger by a third radial distance, and
wherein the third radial distance is greater than the radial distance from the longitudinal axis of the barrel to the internal surface of the barrel near the proximal end of the barrel.

5. The syringe according to claim 4, wherein the third radial distance is approximately equal to the second radial distance.

6. The syringe according to claim 1, wherein a circumferential extent of the second abutment surface is distinct from a circumferential extent of the third abutment surface in a circumferential direction, the circumferential direction being normal to a radial direction about the longitudinal axis of the plunger.

* * * * *